United States Patent
Thorson et al.

(10) Patent No.: US 8,211,654 B2
(45) Date of Patent: Jul. 3, 2012

(54) HIGH-THROUGHPUT ASSAY FOR SUGAR-MEDIATED DRUG TRANSPORT

(75) Inventors: Jon S. Thorson, Middleton, WI (US); John R. Fitzgibbon, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 161 days.

(21) Appl. No.: 12/322,388

(22) Filed: Feb. 2, 2009

(65) Prior Publication Data
US 2009/0317829 A1 Dec. 24, 2009

Related U.S. Application Data

(60) Provisional application No. 61/025,024, filed on Jan. 31, 2008.

(51) Int. Cl.
*G01N 33/53* (2006.01)

(52) U.S. Cl. .......................................... 435/7.2; 435/7.23
(58) Field of Classification Search .................. None
See application file for complete search history.

(56) References Cited

U.S. PATENT DOCUMENTS 5,332,575 A * 7/1994 Redziniak et al. ............ 424/450
7,560,230 B2 * 7/2009 Tidmarsh ..................... 435/6.11

OTHER PUBLICATIONS

Rushfeldt et al (Cancer Research, 1993, 53:658-662).*
Mizuma et al (Biochemical Pharmacology, 1992, 43:2037-2039).*

* cited by examiner

*Primary Examiner* — Laura B Goddard
(74) *Attorney, Agent, or Firm* — Quarles & Brady LLP

(57) ABSTRACT

The invention provides a rapid, quantitative assay to directly assess the impact of a diverse range of sugars upon the sugar-mediated uptake of corresponding sugar-conjugates into various cell types.

4 Claims, 6 Drawing Sheets
(1 of 6 Drawing Sheet(s) Filed in Color)

a)

b)

c)

HIGH-THROUGHPUT ASSAY FOR SUGAR-MEDIATED DRUG TRANSPORT

CROSS-REFERENCE TO RELATED APPLICATIONS

This application claims the benefit of U.S. Provisional Application No. 61/025,024, filed Jan. 31, 2008, the entirety of which is hereby incorporated by reference herein for all purposes.

FIELD OF THE INVENTION

The invention relates generally to methods for generating libraries of small molecule therapeutics. More particularly, the present invention is directed to methods of enzymatic and chemical glycorandomization to rapidly generate and assay libraries of glycoconjugates.

STATEMENT REGARDING FEDERALLY SPONSORED RESEARCH OR DEVELOPMENT

This invention was made with government support under U19 CA113297 awarded by the National Institutes of Health. The Government has certain rights in this invention.

BACKGROUND OF THE INVENTION

The treatment and cure of cancer remains one of the greatest challenges of modern medicine. The war on cancer first began with the use of surgical strategies and radiation therapy. However, the general inability of these early approaches to eradicate metastatic cancers revealed a need for alternative tactics. As a result, small molecule- and macromolecular-based chemotherapeutic compounds have become an essential element in today's anticancer arsenal.

Prompted by the unwanted side effects of many oncolytic drugs, and inspired by Ehrlich's original concept of the 'magic bullet', contemporary anticancer drug development has focused on enhancing drug selectivity and specificity through two main strategies—molecular target-based cancer chemotherapy (often referred to as 'targeted therapy') and the use of molecular targeting techniques.

Molecular target-based therapies are based on an in-depth understanding of cancer cell biology. Such drugs are designed to act upon molecular targets specific to a tumor. Despite some of the early successes of targeted therapies, their clinical development has exposed unwanted adverse effects including thrombocytopenia, myelosuppression, hypertension, neutropenia, myalgia, edema, cardiotoxicity and pulmonary toxicity.

Molecular targeting techniques generally provide specificity via tumor-selective binding or uptake of drug conjugates as mediated by tumor-specific surface epitopes or transporters. Anticancer molecular targeting strategies employ an extensive array of small molecule- (e.g., folates, carbohydrates, peptides) or macromolecule- (e.g., monoclonal antibodies) conjugates and can provide specificity on an intracellular compartmental-, specific cell-type- and/or even at the whole organ-level. Examples include the oligopeptide transporter-mediated uptake of bestatin, the folate receptor-based enhancement of tumor specificity of folate-anticancer drugs, and the ability of organic anion transporters to boost hepatic uptake of anticancer-bile acid drug conjugates.

While molecular-targeted drugs have displayed both successes and limitations, a notable advantage of identifying a successful molecular targeting modality is its potential general applicability to a wide range of therapeutic agents (i.e., a successful tumor-directing small molecule can be conjugated to a variety of anticancer agents to enhance their tumor-specificity). Thus, molecular-targeting techniques offer a greater likelihood to develop broadly applicable platforms for modulating the selectivity, specificity, absorption, distribution, metabolism and excretion of a wide range of anticancer agents (including both conventional cytotoxics/cytostatics as well as newer targeted therapies).

Chemoenzymatic glycorandomization employs the inherent or engineered substrate promiscuity of sugar-activating enzymes, coupled with inherently promiscuous natural product glycosyltransferases (GTs), to provide a robust chemoenzymatic means to glycodiversify natural product-based scaffolds. Chemoenzymatic glycorandomization has been successfully applied toward antibiotic scaffolds (novobiocin, erythromycin/megalomicin, vancomycin), anticancer models (rebeccamycin/staurosporine/AT2433 and calicheamicin) and antihelmenthics (avermectin/ivermectin).

In contrast, neoglycorandomization relies upon the installation of a uniquely reactive methoxyamine 'handle' followed by a direct reaction with free sugars. Neoglycorandomization is a groundbreaking advance over classical chemical glycosylation strategies (which require extensive steps for sugar/aglycon protection/deprotection and sugar activation) and allows for extensive neoglycorandomized natural product libraries in essentially a single step.

While enzymatic glycorandomization is restricted to the inherent specificity of the natural GTs employed, neoglycorandomization can be accomplished essentially anywhere the methoxyamine handle can be installed. This allows one to expand beyond natural positions of glycosylation to explore the potential benefits of glycosylating even non-glycosylated natural products and therapeutics.

Therefore, a need exists for compositions and methods for rapidly identifying and assessing compounds which can enhance the tumor-specific uptake of drug-conjugates.

SUMMARY OF THE INVENTION

Herein, the inventors provide a systematic platform for rapidly assessing the specific role of a diverse range of sugars to enhance tumor-specific uptake of sugar-conjugates and, in parallel, their impact upon the selectivity of a representative set of cytotoxic drugs.

The present invention provides a method for assaying sugar-mediated transport of glycoconjugates contained in a glycorandomized library. The method comprises providing a glycorandomized library comprising glycoconjugates with different attached sugars; contacting each of said glycoconjugates with cells under conditions to allow uptake of the glycoconjugates into the cells; and assessing uptake of said glycoconjugates into the cells, wherein sugar-mediated transport of the glycoconjugates into the cells is quantified relative to a corresponding conjugate lacking the attached sugars. The glycoconjugates are contacted with cells independently and in parallel. In a preferred embodiment the cells are cancerous animal cells, although the method may also be used with bacteria, viruses, parasites and non-cancerous animal cells. The glycoconjugates are preferably sugar-fluorophore conjugates, wherein the sugar-fluorophore is preferably selected from the group consisting of aminofluoroscein, NBD or dansyl chloride.

The invention also provides a method of assaying tumor selectivity for sugar-mediated transport of glycoconjugates contained in a glycorandomized library. The method comprises providing a glycorandomized library containing glycoconjugates differing by attached sugars; contacting each of said glycoconjugates with cells of a first line under conditions to allow uptake of the glycoconjugates into the cells; assessing uptake of said glycoconjugates into the cells wherein sugar-mediated transport of the glycoconjugates into the cells is quantified relative to a corresponding conjugate lacking the attached sugars; repeating steps (a)-(c) with cells of a second, differing cell line; and comparing sugar-mediated transport of said glycoconjugates between cells of the first line and the second cell line, wherein cell line selectivity for sugar-mediated transport of said glycoconjugates is indicated by elevated sugar transport activity in one of the cell lines relative to the other cell line.

The invention also provides a kit for assaying sugar-mediated transport of glycoconjugates contained in a glycorandomized library, comprising a glycorandomized library comprising glycoconjugates with different attached sugars; cells of a first line; and instructions for use. In an alternative embodiment, the invention provides a kit for assaying tumor selectivity for sugar-mediated transport of glycoconjugates contained in a glycorandomized library, the kit comprising a glycorandomized library containing glycoconjugates differing by attached sugars; cells of a first line; cells of a second, differing line; and instructions for use.

A fundamental advantage of the present invention is to provide a rapid, quantitative assay to directly assess the impact of a diverse range of sugars upon the uptake of sugar-drug conjugates by GLUT transporters.

Another fundamental advantage of the present invention is the development of a unique probe set and assay that enables the discovery of atypical sugars which impart significantly enhanced tumor uptake and specificity of a sugar-drug conjugate, as compared to the standard sugar-drug conjugates of the prior art, such as glucose, 2-deoxyglucose or fluorodeoxyglucose (FDG).

Other objects, features and advantages of the present invention will become apparent after review of the specification, claims and drawings.

PETITION FOR COLOR DRAWINGS

The patent or application file contains at least one drawing executed in color. Copies of this patent with color drawing(s) will be provided by the U.S. Patent and Trademark Office upon request and payment of any necessary fee.

DETAILED DESCRIPTION OF THE INVENTION

I. In General

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by any later-filed nonprovisional applications.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. The Invention

Herein, the inventors provide a versatile method for producing large quantities of tumor-specific small molecule therapeutics which differ solely by their attached sugars. The method also allows the identification of tumor-specific therapeutics which exhibit increased rates of uptake by the tumor. The chemoenzymatic- and neo-glycorandomization of molecules for the rapid generation of libraries of small molecule therapeutics which differ solely by their attached sugars is the foundation of this invention.

Figure 1:
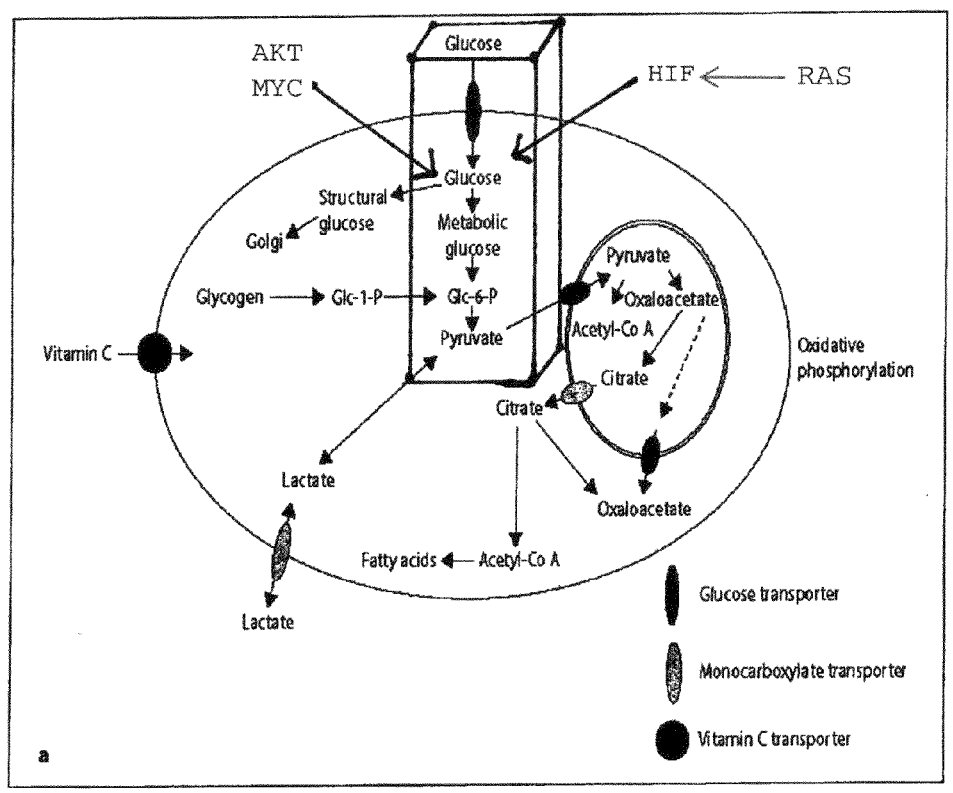
FIG. 1. Illustration of the Warburg effect.

Cancer cells typically exhibit increased levels of glucose uptake and glycolysis, despite reduced levels of oxygen consumption (FIG. 1). In most cells, facilitative glucose uptake is mediated by GLUT proteins. Intracellular glucose is accumulated in two distinct pools—the metabolic pool used for glycolysis and the structural pool used for the synthesis of glycoproteins and extracellular matrix macromolecules. Under aerobic conditions, oxidative phosphorylation ensures sufficient ATP production while under anaerobic conditions glycolysis predominates. The Warburg effect leads to the enhanced conversion of glucose to lactate by tumor cells (box), even in the presence of adequate oxygen (normally used for oxidative phosphorylation). Relevant to the present invention, the activation of the AKT oncogene results in increased glucose transportation and stimulation of hexokinase HK2 activity, which enhances glycolytic rates. In a tumor cell, HIF-1 (hypoxia-inducible factor), increased by RAS and loss of VHL (von Hippel Lindau protein—which normally mediates HIF degradation) and stabilized by hypoxia, also transactivates glycolytic genes, including the expression of sugar transporters.

Unlike normal cells, tumors display a vast increase in glucose uptake and consumption, a reliance on the glycolytic pathway for ATP production and, as a result, an increased production of lactate. This altered metabolic profile in tumors and, more specifically, the corresponding enhanced sugar uptake by said tumors, provides an immediate pathway for the targeted tumor-specific molecules of the present invention.

The present invention provides a method for assaying sugar-mediated transport of glycoconjugates contained in a glycorandomized library. The method comprises providing a glycorandomized library comprising glycoconjugates with different attached sugars; contacting each of said glycoconjugates with cells under conditions to allow uptake of the glycoconjugates into the cells; and assessing uptake of said glycoconjugates into the cells, wherein sugar-mediated transport of the glycoconjugates into the cells is quantified relative to a corresponding conjugate lacking the attached sugars.

By "glycoconjugate," we mean any compound or molecule that is covalently bound to a glycosidic residue. The compounds may include compositions of matter having biological, therapeutic and/or diagnostic activity in animals which include, but are not limited to: antiviral agents such as acyclovir, zidovudine and the interferons; antibacterial agents such as aminoglycosides, cephalosporins and tetracyclines; antifungal agents such as polyene antibiotics, imidazoles and triazoles; antimetabolic agents such as folic acid analogues, folic acid antagonists including methotrexate, and purine and pyrimidine analogs; antineoplastic agents such as the anthracycline antibiotics and plant alkaloids; sterols such as cholesterol; carbohydrates, e.g., sugars and starches; amino acids, peptides, proteins such as cell receptor proteins, immunoglobulins, enzymes, hormones, neurotransmitters and glycoproteins; dyes; radiolabels such as radioisotopes and radioisotope-labeled compounds; radiopaque compounds; fluorescent compounds; mydriatic compounds; bronchodilators; local anesthetics; nucleic acid sequences such as messenger RNA, cDNA, genomic DNA and plasmids; bioactive lipids such as ether lipids and ceramides; and the like.

By "library," we mean a mixture of glycoconjugates of varying sequences which can be subjected to a screening procedure to identify compounds or molecules that exhibit enhanced sugar-mediated transport.

The glycoconjugates are contacted with cells independently and in parallel. In a preferred embodiment the cells are cancerous animal cells, although the method may also be used with bacteria, viruses, parasites and non-cancerous animal cells.

The glycoconjugates are preferably sugar-fluorophore conjugates, wherein the sugar-fluorophore is selected from the group consisting of aminofluoroscein, NBD or dansyl chloride. By "fluorophore" we mean a compound that can absorb electromagnetic energy and is capable of at least partially remitting some fraction of that energy as electromagnetic radiation over some time period. Suitable fluorophores include, but are not limited to, coumarins and related dyes, xanthene dyes such as fluoresceins, rhodols, and rhodamines, resorufins, cyanine dyes, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, semiconductor fluorescent nanocrystals, fluorescent proteins and fluorescent europium and terbium complexes and related compounds. Fluorophores may also be environmental sensitive or be indicators of various ions such as calcium, magnesium or pH, as is known in the art.

Preferred fluorophores typically exhibit good quantum yields, lifetimes, and extinction coefficients, are resistant to collisional quenching and bleaching, and should preferably be easily conjugated to the sugar. Particularly desirable are fluorophores that show absorbance and emission in the red and near infrared range, which are useful in whole animal studies, because of reduced scattering background fluorescence, and greater transmission through tissues. Preferred examples include nitrobenzoxadiazole (NBD) or 5-(dimethylamino)naphthalene-1-sulfonyl chloride.

By "enhanced," we mean an increased rate of transport into the cell line as compared to the rate of transport into the cell line via an unmodified sugar-drug conjugate.

The invention also provides a method of assaying tumor selectivity for sugar-mediated transport of glycoconjugates contained in a glycorandomized library. The method comprises providing a glycorandomized library containing glycoconjugates differing by attached sugars; contacting each of said glycoconjugates with cells of a first line under conditions to allow uptake of the glycoconjugates into the cells; assessing uptake of said glycoconjugates into the cells wherein sugar-mediated transport of the glycoconjugates into the cells is quantified relative to a corresponding conjugate lacking the attached sugars; repeating steps (a)-(c) with cells of a second, differing cell line; and comparing sugar-mediated transport of said glycoconjugates between cells of the first line and the second cell line, wherein cell line selectivity for sugar-mediated transport of said glycoconjugates is indicated by elevated sugar transport activity in one of the cell lines relative to the other cell line.

The invention also provides a kit for assaying sugar-mediated transport of glycoconjugates contained in a glycorandomized library, comprising a glycorandomized library comprising glycoconjugates with different attached sugars; cells of a first line; and instructions for use. In an alternative embodiment, the invention provides a kit for assaying tumor selectivity for sugar-mediated transport of glycoconjugates contained in a glycorandomized library, the kit comprising a glycorandomized library containing glycoconjugates differing by attached sugars; cells of a first line; cells of a second, differing line; and instructions for use.

Figure 2:
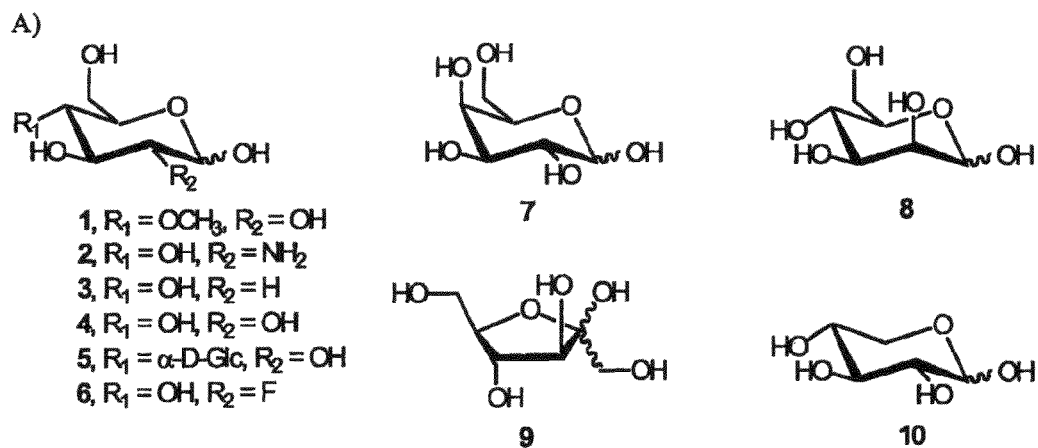
FIG. 2. (a) Structures of representative carbohydrates employed in GLUT substrate-specificity studies. The sugars represented include: 3-O-methylglucose, 1; glucosamine, 2; 2-deoxyglucose, 3; glucose, 4; maltose, 5; 2-fluoroglucose, 6; galactose, 7; mannose, 8; fructose, 9; and xylose, 10. (b) Models for the orientation of facilitative glucose transporter proteins in the cell membrane. Transmembrane domains (TM) are labeled 1 to 12. The sites of glycosylation (N) are shown. Conserved domains and amino acids are also included. For class I transporters, the TMs proposed to form the glucose transport channel are highlighted by gradient shading, and regions which interact with hexose substrates and the GLUT inhibitor cytochalasin B are indicated.
Figure 2:
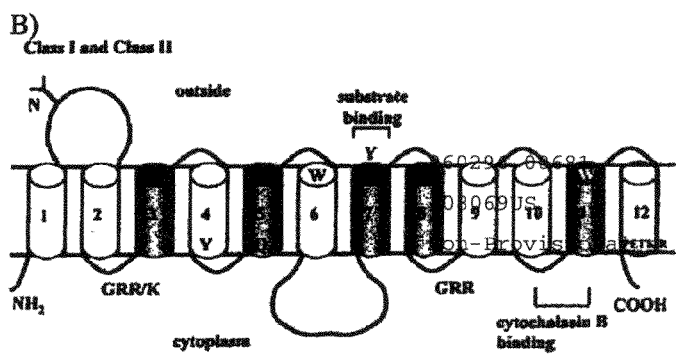
Figure 3:
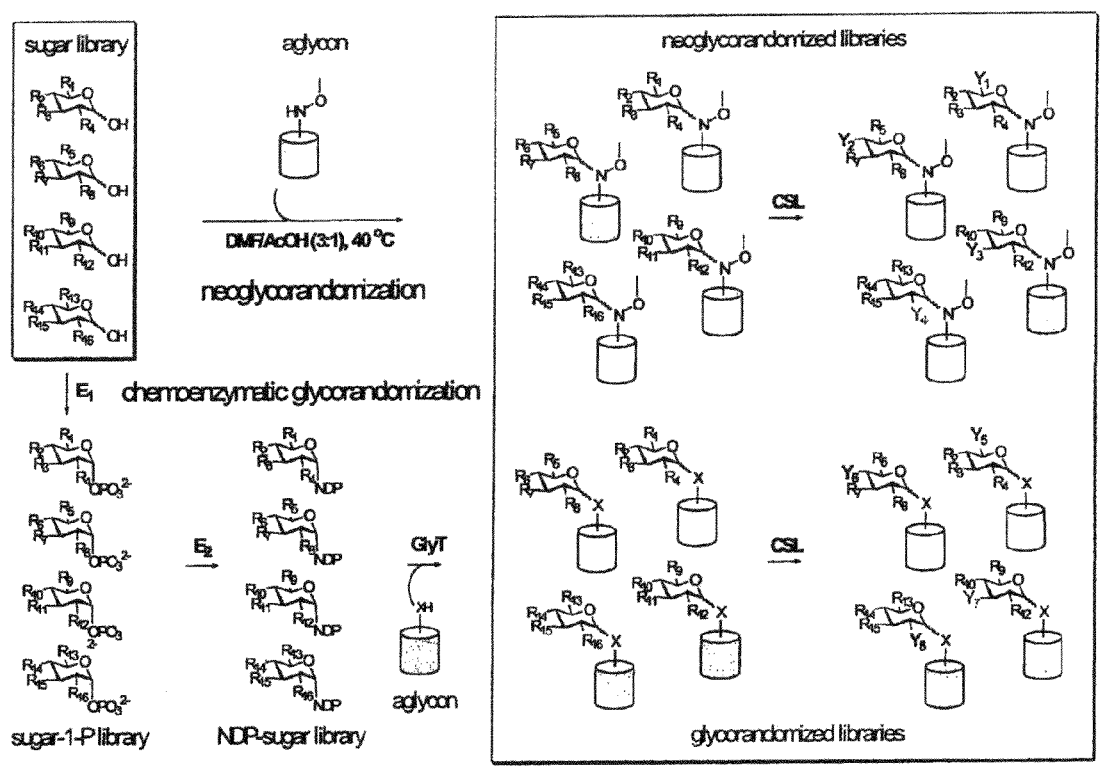
FIG. 3. An overview of the complementary enzymatic (bottom) and chemical (top) glycorandomization strategies. $E_1$, an evolved sugar kinase; $E_2$, an engineered promiscuous nucleotidylyltransferase; GlyT, a natural product glycosyltransferase; CSL, chemoselective ligation reactions (e.g. Huisgen 1,3-dipolar cycloaddition). The focus of this proposal is to utilize neoglycorandomization (top) to rapidly generate differentially-glycosylated lipoglucopeptides (from vancomycin) and screen them for various anti-infective activities.

The facilitative and sodium-dependent glucose transport processes of cells are mediated by two distinct families of structurally-related glucose transporters (Table 1). The passive, facilitative glucose transporters (GLUTs) allow the energy independent transport of glucose across the hydrophobic cell membrane and down its concentration gradient. Thirteen members of this family have been identified, GLUT1-12 and HMIT ($H^+$/myo-inositol transporter) and sequence comparison suggests structural conservation exists throughout the entire family (FIG. 2).

Based upon phylogenetic analysis, the GLUT family has been divided into three classes. Class I (48-63% identity) includes the well-characterized GLUT1-4. Class II (36-40% identity) contains the fructose transporter GLUT5 and three recently described proteins GLUT7, 9 and 11. Class III (19-41% identity) is composed of newer members GLUT6, 8, 10, 12 and HMIT.

A model for the orientation of GLUTs in the cell membrane has been proposed based upon the amino acid sequences of GLUTs (FIG. 2b). Based upon this model, GLUTs transverse the cell membrane twelve times with 12-helical transmembrane (TM) domains and the $NH_2$— and COOH-termini both terminate on the cytoplasmic side of the membrane. A high degree of homology exists between GLUT proteins across the TM domains with significant variation limited primarily to loop and $NH_2$/COOH— terminal sequences.

Two major distinctions among classifications emerge from this analysis. First, the class I and II members of this family have a large extracellular loop between TMs 1 and 2, the glycosylation of which modulates the efficiency of glucose transport. In contrast, the class III members contain a large extracellular loop between TMs 9 and 10 which carries putative N- and O-glycosylation motifs. Second, class II members lack the tryptophan residue within the GPGPIPW motif of TM10 critical for binding the inhibitory ligands cytochalasin B and forskolin.

Based upon expression profiling and/or Western blotting, many GLUT transporters have unique tissue distribution. These distinctions in tissue distribution, along with the differences in substrate specificities provide the basis for functional assignment (Table 1). Among transporters, GLUT1 is the most ubiquitously distributed isoform and is involved in basal glucose uptake. GLUT2 expression occurs mainly in kidney and intestinal epithelial cells, where it participates in the release of absorbed glucose, and it also provides glucose-sensing functions for insulin secretion in pancreatic γ-cells. GLUT3 is considered to be the neuron-specific transporter while GLUT4 is predominately expressed in insulin sensitive tissues.

Under insulin stimulation, GLUT4 undergoes a rapid intracellular-to-cell surface translocation, resulting in a dramatic increase in cellular glucose transport activity. GLUT5 is considered to be responsible for most of the fructose uptake in the small intestine and GLUT7, most closely related to GLUT5, is distributed predominately in the small intestine and colon. GLUT8 is unique as it more closely resembles hexose transporters found in plants and bacteria. GLUT8, which may also undergo an intracellular-to-cell surface translocation, has been postulated to play a major role in providing glucose to mature spermatozoa. GLUT9 is primarily detected in the kidney and the liver and at least three isoforms are known to be upregulated in diabetes. GLUT10 is expressed at highest levels in the liver and pancreas but basal GLUT10 expression has also been detected in a variety of other tissues.

GLUT10 has received special interest because of its link to the human chromosomal region 20q12-13.1 (a susceptibility locus for Type 2 diabetes). Isoforms of GLUT11, another transporter with significant similarity to GLUT5, have been found in a variety of tissues. GLUT12 was initially cloned from breast cancer tissue and its expression appears to be restricted to insulin-sensitive tissues. Little is known regarding the tissue distribution of GLUT6.

Substrate specificities (FIG. 2a) for many of the GLUT transporters have been established via expression of single isolated GLUTs in 'GLUT-free' systems. Transfected *Xenopus* oocytes have served as the predominate model systems in this regard but COS-7, CHO and yeast variants have also been employed. Notably, substrate specificity studies to date have been primarily restricted to the availability of radio-labeled carbohydrates (e.g., [U-$^{14}$C]fructose, 2-deoxy-D-[2,6-$^3$H] glucose, D-[2,6-$^3$H]glucose) where alternative 'substrates' are often identified through their ability to inhibit the transport of one of these standard radio-labeled agents (e.g. in these cases, the 'affinity' is actually a measurement of $K_i$, not a direct measure of transport).

From a combination of such general methods and models, GLUT1 specificity studies revealed low affinity (greater than 15 mM) for 3-O-methylglucose, galactose, mannose and glucosamine and high affinity (approximately 3-5 mM) for 2-deoxyglucose and glucose. GLUT2 specificity studies revealed low affinity (greater than 15 mM) for glucose, galactose, mannose and fructose but high affinity (approximately 1 mM) for glucosamine. GLUT3 transports glucose and 2-deoxyglucose with high affinity (approximately 1.5 mM) and a variety of carbohydrates (including galactose, mannose, maltose, and xylose) with moderate to low affinity (greater than 8.5 mM). GLUT4 displays high affinity (less than or equal to 5 mM) for both glucose and glucosamine. Conversely, GLUT5 has little or no affinity for glucose, but instead has a high affinity for fructose (approximately 1 mM). GLUT7, while most closely related to GLUT5, has high affinity (greater than 0.5 mM) for both glucose and fructose but does not transport galactose, 2-deoxy-D-glucose or xylose. GLUT8 also displays high affinity (approximately 2 mM) for glucose while GLUT9 exhibits glucose and 2-deoxy-glucose transport.

GLUT10 displays high affinity (greater than 0.5 mM) for both glucose and galactose while GLUT11 provides for transport of fructose and glucose, but not galactose. GLUT12 displays preferential affinity for glucose over other hexoses. Little is known regarding the specificity of GLUT6.

In addition to the limitations of GLUT substrate specificity assays, such methods cannot be used to directly assess the ability of GLUT transporters to facilitate the uptake of sugar-drug conjugates. Therefore, a fundamental advantage of the present invention is to provide a rapid, quantitative assay to directly assess the impact of a diverse range of sugars upon the uptake of sugar-drug conjugates by GLUT transporters.

Nearly all tumors over-express GLUT family members (Table 1) normally expressed in the respective tissues of origin, most notably GLUT1. In some cases, tumors can also induce expression of GLUTs not normally expressed in the respective tissue of origin. Overexpression of GLUT1 has been widely observed in tumors (bladder, brain, breast, cervical, colorectal, cutaneous squamous cell, embryonic, esophageal, gastric, head and neck, leiomyosarcomas, lung, liver, ovarian, pancreatic, penile, thyroid, uterine, and vascular hemangiomas) and, in most cases reported, the level of GLUT1 overexpression correlates with metastasis and/or poor prognosis. GLUT5 has been found to be expressed in malignant breast cells but not in normal breast cells and blocking GLUT5 expression has been shown to reduce the growth of malignant cancerous cells. GLUT4 and GLUT12 overexpression has also been observed in breast tumors and, in the case of GLUT4, also in gastric and lung cancers.

demonstrated lower myelotoxicity and a higher antitumor activity than the parent ifosfamide. In glufosfamide, the glucose moiety stabilizes the drug and provides for preferential uptake via sugar transporters.

TABLE 1

Facilitative GLUT Transporters

| Protein | Class | Isoform[a] | $K_m^b$ | Distribution | Proposed Function | Overexpression in human cancer[c] |
|---|---|---|---|---|---|---|
| GLUT1 | I | 492 | 3-7 | Ubitquitous distribution | Basal glucose uptake | Bladder (A), brain (A), cutaneous squamous cell (NR), embryonic (NR), esophageal (NA), gastric (A), head and neck (A), leiomyosarcomas (A), lung (A), ovarian (A), pancreatic (NR), penile (NR), thyroid (A), uterus (NR), vascular-hemangioma (NR) |
| GLUT2 | I | 524 | 17 | Liver, islets, kidney, small intestine | High capacity, low affinity transport | Gastric (A) |
| GLUT3 | I | 496 | 1.4 | Brain and nerve cells | Neuronal transport | Brain (A), breast (NR), gastric (NR), head and neck (NA), lung (A), meningiomas (NR), ovarian (NR) |
| GLUT4 | I | 509 | 6.6 | Muscle, fat, heart | Insulin-regulated transport | Breast (NR), gastric (NR), lung (NR) |
| GLUT5 | II | 501 | _d | Intestine, kidney, testis | Fructose transport | Lung (A) |
| GLUT7 | II | 524 | .3 | Small intestine, colon, testis | Fructose transport | |
| GLUT9 | II | 511/540 | N.D.[e] | Liver, kidney | N.D.[e] | |
| GLUT11 | II | 496 | N.D.[e] | Heart, muscle | Fructose transport | |
| GLUT6 | III | 507 | N.D.[e] | Spleen, leukocytes, brain | N.D.[e] | |
| GLUT8 | III | 477 | 2 | Testis, blastocyst, brain, muscle, adipocytes | Fuel supply for spermatozoa, insulin-responsive transport in blastocysts | |
| GLUT10 | III | 541 | .3 | Liver, pancreas | N.D.[e] | |
| GLUT12 | III | 617 | N.D.[e] | Heart, prostrate, mammary gland | H+/myo-inositol co-transport | Breast (NR) |
| HMIT | III | 618/629 | N.D.[e] | brian | | |

[a]number of amino acids;
[b]millimolar (mM);
[c]'A' indicates an association between overexpression and metastatis/poor prognosis,
'NA' indicates no association between overexpression and metastatis/poor prognosis has not been reported;
[d]not a substrate;
[e]not determined.

Such observations present the opportunity to exploit GLUT-dependent strategies in cancer treatment and diagnostics. One such early study was to attempt to use 2-deoxyglucose or 5-thioglucose as antimetabolites to interfere with the glycolytic dependency of tumors. More recent work has focused upon the generation of glucose-conjugates. Examples of this approach include 2-GluSNAP, a glucose-conjugated nitric oxide donor which has shown promise in ovarian carcinoma.

In a similar manner, glucose-conjugated $O^6$-methylguanine-DNA methyltransferase inhibitors (a major determinant of resistance to alkylating antitumor agents) presented selective activity enhancements. Improvements upon oxaliplatin via glucose conjugation have also been recently reported. Perhaps the most notable example is the glucose-conjugate of oxazaphosphorine ifosfamide (glufosfamide) which has For cancer diagnostics/imaging, the most widely used tumor positron emission tomography (PET) imaging agent is [$^{18}$F]fluorodeoxyglucose (FDG).[29] FDG (FIG. 2a, 6) is transported, phosphorylated and metabolically trapped in tumor cells as a glucose surrogate. The overexpression of GLUT transporters, and glycolytic enzymes such as hexokinase, in tumors enable the tumor-selective imaging with FDG. The demonstrated success of both glucose surrogates and glucose-conjugates in cancer imaging and treatment provide validation for GLUT-dependent cancer-targeting strategies.

A fundamental advantage of the present invention is the development of a unique probe set and assay that enables the discovery of atypical sugars which impart significantly enhanced tumor uptake and specificity of a sugar-drug conjugate, as compared to the standard sugar-drug conjugates of the prior art, such as glucose, 2-deoxyglucose or FDG.

Kits. In an alternate embodiment of the invention, a kit for assaying sugar-mediated transport of glycoconjugates contained in a glycorandomized library according to the present invention is provided. In one embodiment the kit includes a glycorandomized library comprising glycoconjugates with different attached sugars; cells of a first line; and instructions for use.

In another embodiment, the present invention provides a kit for assaying tumor selectivity for sugar-mediated transport of glycoconjugates contained in a glycorandomized library. In one embodiment the kit includes a glycorandomized library comprising glycoconjugates with different attached sugars; cells of a first line; cells of a second, differing line; and instructions for use.

By "instructions for use" we mean a publication, a recording, a diagram, or any other medium of expression which is used to communicate the usefulness of the invention for one of the purposes set forth herein. The instructional material of the kit can, for example, be affixed to a container which contains the present invention or be shipped together with a container which contains the invention. Alternatively, the instructional material can be shipped separately from the container or provided on an electronically accessible form on a internet website with the intention that the instructional material and the biocompatible hydrogel be used cooperatively by the recipient.

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

III. EXAMPLES

Example 1

Synthesis of a Fluorescence-Based Sugar Transporter Probe Library

Figure 4:
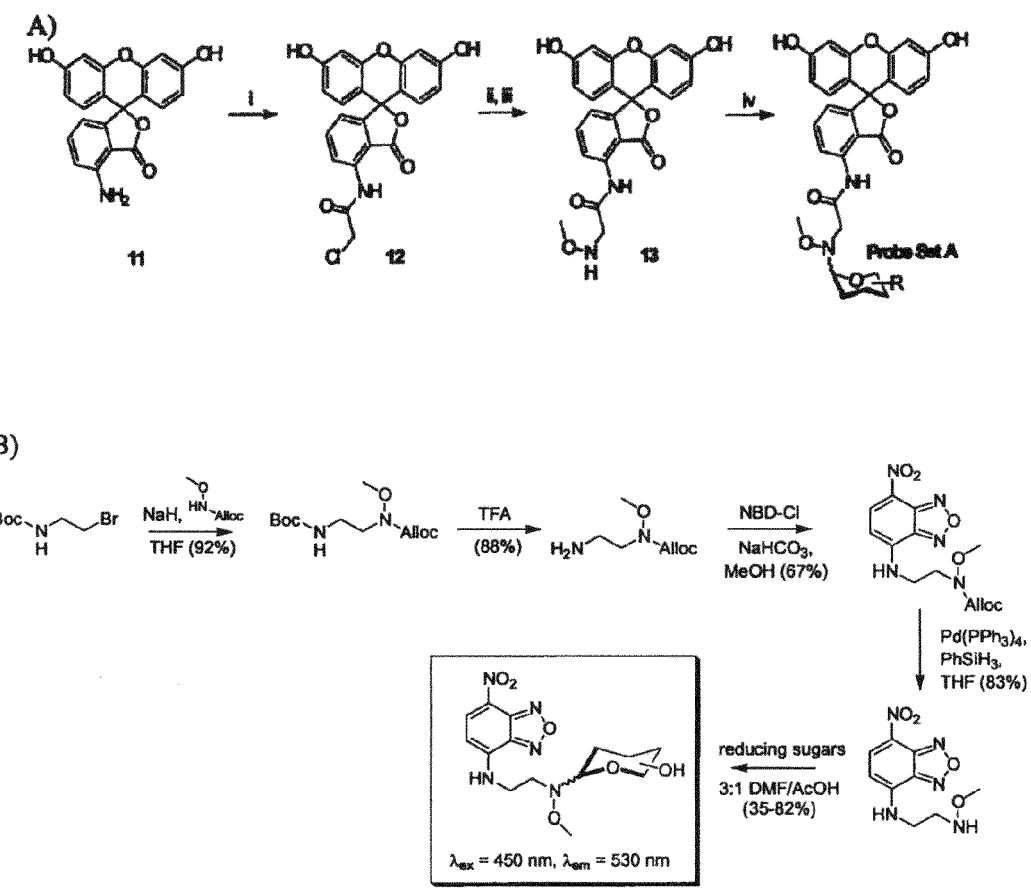
FIG. 4. (a) Synthesis of sugar transporter 'Probe Set A' (i) 1.5 eq DIEA, 1.5 eq chloroacyl chloride, dry THF, 24 h (75%); (ii) 3 eq NaI, MeOH, 2 h (95%); (iii) 5 eq $NH_2OMe$, sealed vial, 45° C., 24 h (85%); (iv) 2 eq reducing sugar, 3:1 DMF:AcOH, 45 C, 48 h (25-60%, 40 analogs total). (b) Synthesis of sugar transporter 'Probe Set B'.

To directly assess the impact of sugars upon the specificity and efficiency of cellular uptake of glycoconjugates, the inventors synthesized a neoglycorandomized sugar transporter probe (FIGS. 4A & b, Probe Set A and Probe Set B) containing several distinct members differing solely by the sugars attached. By "probe" we mean a compound useful as marker or environmental indicator, or modifying reagent for use with the present invention. Probes may comprises fluorescent, spectroscopic or modifying moieties as described herein. The different sugars used can be seen in Table 2.

TABLE 2

Sugars used in the sugar-drug conjugates of the present invention.

| | |
|---|---|
| D-lyxoside | D-lactoside |
| 6-deoxy-D-glucoside | L-rhamnoside |
| 3-deoxy-D-glucoside | D-maltoside |
| D-xyloside | N-acetyl-D-glucosaminoside |
| D-riboside | D-cellobioside |
| 2-deoxy-D-galactoside | 6-deoxy-6-chloro-D-galactoside |
| L-lyxoside | 6-deoxy-6-bromo-D-galactoside |
| L-glucoside | 6-deoxy-6-azido-D-galactoside |
| D-fucoside | 4-deoxy-4-azido-D-glucoside |
| L-mannoside | D-glucorono-6,3-lactonide |
| D-alloside | 2-deoxy-2-amino-D-glucoside |
| L-galactoside | 3-O-methyl-D-glucoside |
| maltotrioside | 2,3,4-tri-O-acetyl-L-rhamnoside |
| L-fucoside | mycaroside |
| D-glucuronoside | 2,3,4,6-tetra-O-benzyl-D-glucopyranoside |

TABLE 2-continued

Sugars used in the sugar-drug conjugates of the present invention.

| | |
|---|---|
| 2-deoxy-D-glucoside | 2,3,4-tri-O-benzyl-L-fucopyranoside |
| L-xyloside | 2,3,5-tri-O-benzyl-D-arabinofuranoside |
| 3-amino-3-deoxy-L-xyloside | 2,3,5-tri-O-benzyl-D-ribofuranoside |
| 3-azido-3-deoxy-L-xyloside | 6-deoxy-6-fluoro-D-glucoside |
| 3-thio-3-deoxy-L-xyloside | 4-O-(□-D-galacto pyranosyl-D-mannopyranoside) |
| D-Galacturonoside | 6-deoxy-6-acyl-D-galactoside |
| 2-deoxy-L-riboside | L-taloside |
| D-arabinoside | 6-thio-D-mannose dimer |
| 2-deoxy-D-riboside | 6-deoxy-6-N-decanoyl-D-glucosaminoside |
| L-riboside | 3-deoxy-3-N-decanoyl-D-glucosaminoside |
| D-melibioside | 3-deoxy-3-carbamic acid allyl ester-D-glucoside |
| D-altroside | 6-deoxy-3-carbamic acid allyl ester-D-glucoside |
| L- arabinoside | 2,3,4,6-tetra-O-benzyl-D-mannopyranoside |
| D-mannoside | 3-deoxy-3-azido-D-glucoside |
| N-acetyl-D-galactosaminoside | D-Digitoxoside |
| novioside | 6-deoxy-6-amino-D-glucoside |
| L-alloside | D-galactoside |
| D-taloside | 6-deoxy-6-thio-acyl-D-galactoside |
| L-altroside | D-idoside |
| 3-fluoro-3-deoxy-D-glucoside | L- idoside |
| 2-fluoro-2-deoxy-D-glucoside | D-guloside |
| N-acetyl-D-mannosaminoside | D-glucoside |

Figure 5:
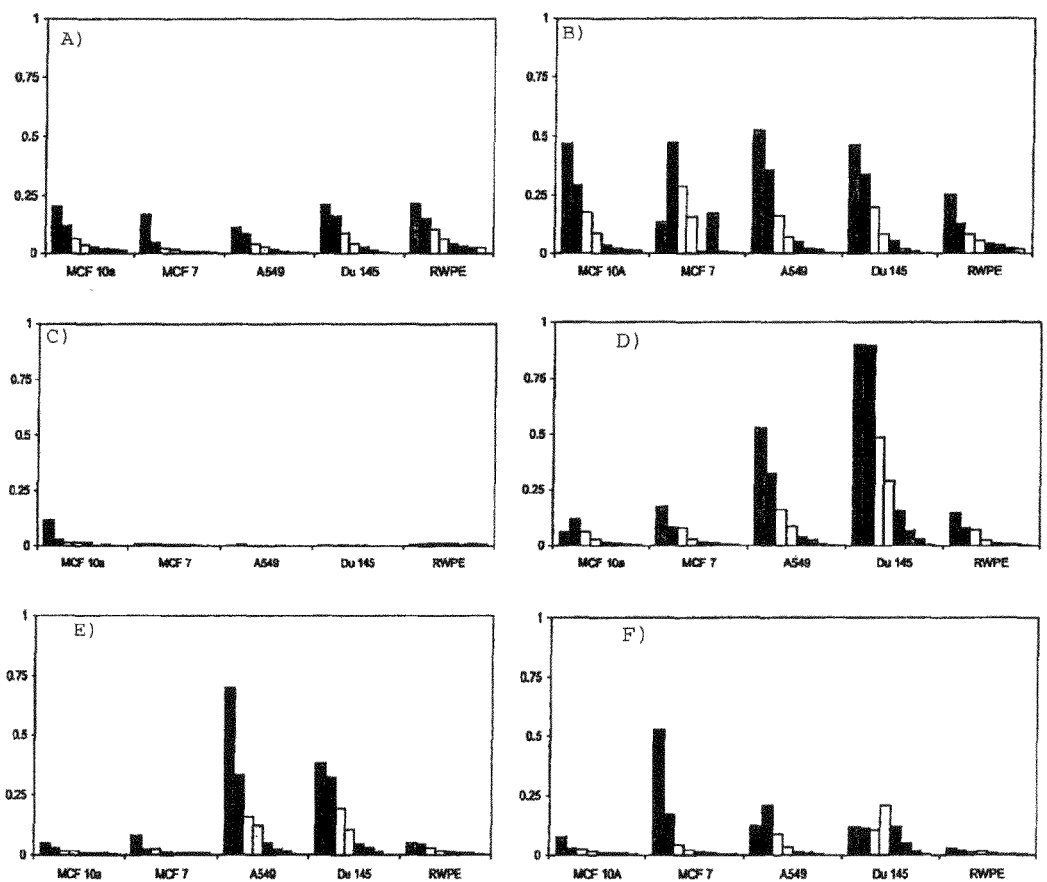
FIG. 5. Representative sugar transporter assays. Cell lines used for sugar transporter assays include MCF10A (immortalized breast), MCF7 (breast cancer), A549 (non-small cell lung cancer), Du145 (prostate cancer), RWPE (immortalized prostrate); (A) D-glucose-conjugate; (B) L-glucose-conjugate; (C) N-acetyl-D-mannose-conjugate; (D) D-glucuronic acid-conjugate; (E) L-allose-conjugate; (F) L-xylose-conjugate. For each cell line, the dose range was 250 µM, 125 µM, 62.5 µM, 31.3 µM, 15.6 µM, 7.8 µM, 3.9 µM and 0 µM. The average error (40 compounds, 5 cell lines) was 8.3%. No uptake was observed with parent 11 or aglycon 13 (data not shown).

The library synthesis was accomplished in four simple steps with an overall yield of 15-37% starting from commercially-available aminofluoroscein (FIG. 5a, 11). All members were purified by solid phase extraction to provide a library with an average purity greater than or equal to 93%.

In contrast to the few prior reports of sugar-fluorophore conjugates (limited to D-glucose, D-glucosamine, 2-deoxy-D-glucose, 2-deoxyfluoroglucose, galactose and fructose), the neoglycosyl chemistry of the present invention enables the rapid synthesis of large probe libraries by eliminating most of the tedious protection, deprotection and anomeric activation steps associated with conventional glycosylation strategies.

In addition, as additional comparators to the D-glucose 'standard', the 2-deoxy-D-glucose probe displayed similarly broad specificity but slightly lower uptake levels, while the FDG probe also displayed slightly lower uptake levels but a preference for the prostrate and non-small cell lung cell lines (data not shown).

Example 2

Sugar Transport Assay

For the sugar transporter assay of the present invention, cells were plated at a density of 30,000 cells/ml (100 μL/well) in a 96-well clear bottom microtiter plates. Cells were allowed to attach overnight, and then incubated in glucose-free medium for an additional 24 hours. Compounds were added (from 96-well compound stock plates at a 1:100 dilution) using a Biomek FX liquid handler equipped with a 96 channel head. The plates were incubated for 1 hour and then the compound solution was removed by gentle aspiration. The cells were subsequently washed (1×100 μL) with phosphate buffered saline to remove residual fluorescent dye.

Figure 6:
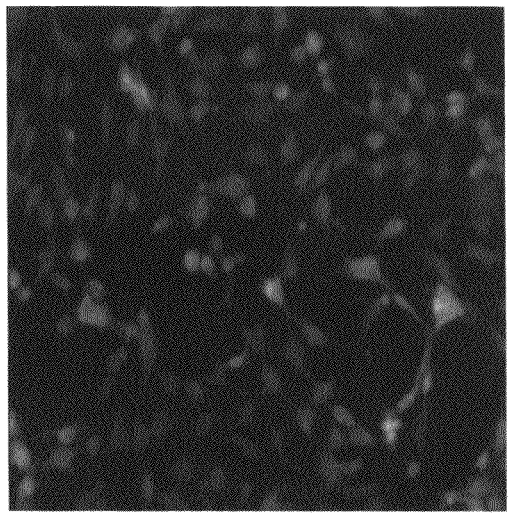
FIG. 6. Fluorescence microscopy of sugar uptake in non-small cell lung cancer cells (A549). (a) no sugar transporter probe (negative control); (b) D-altrose conjugate; (c) D-allose conjugate. For all three panels, general cell-staining was accomplished with 1 µM Calcein Red and imaged on an Olympus IX81 inverted microscope at 20× magnification.
Figure 6:
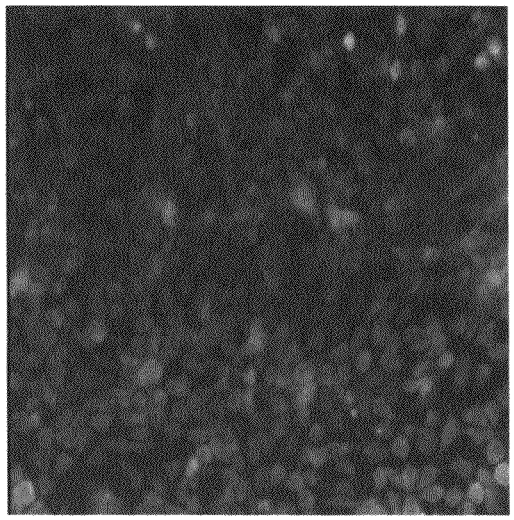
Figure 6:
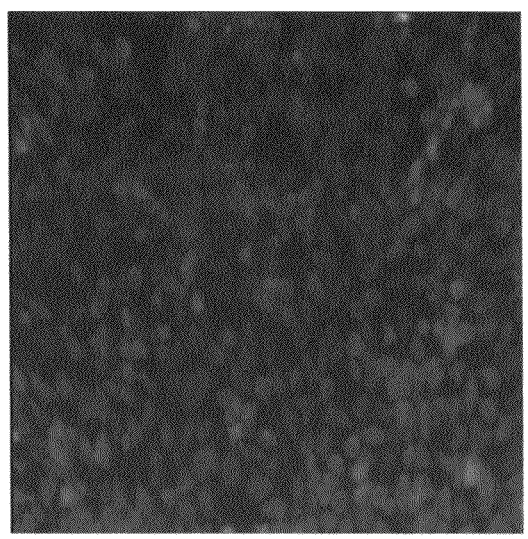

Sugar-conjugate uptake was assessed via intracellular fluorescence (FIG. 4b-4f) as determined using a Safire2™ multi-mode microplate reader ($\delta_{ex}$=485 nm, $\delta_{em}$=535 nm) and normalized to cell number by a subsequent CellTiter-Glo® luminescent cell viability assay. For the CellTiter-Glo® luminescent cell viability assay, 50 μL of CellTiter-Glo® detection reagent was added to each well of the 96 well plate and the plates were incubated for 10 minutes at room temperature with gentle shaking. The CellTiter-Glo® luminescent cell viability assay was analyzed on a Safire2™ multi-mode microplate reader for luminescence at 1 second per well. As an initial preliminary study, the transport assay with a representative set of probes was also analyzed using microscopy (FIG. 6).

The resultant data show that the present invention provides the first example of a systematic approach for rapidly assessing the specific role of a wide range of sugars to enhance the specific uptake of sugar-conjugates and extends well beyond the standard small set of sugars employed in typical sugar transport studies. Most importantly, the inventors' results illustrate that slight perturbations in sugar structure can lead to drastic consequences in terms of in vitro cellular uptake. For instance, the neoglycorandomized L-glucose of the present invention exhibits a non-specific enhancement of overall uptake (FIG. 5B, L-glucose) in comparison to D-glucose (FIG. 5A). Similarly, the neoglycorandomized N-acetyl-D-mannosamine of the present invention exhibits a nearly complete exclusion (FIG. 5C, N-acetyl-D-mannosamine). Further, some neoglycorandomized sugars of the present invention exhibit a tumor-preference—prostrate tumor versus 'normal' prostrate (FIG. 5D, D-glucuronic acid), or non-small cell lung (FIG. 5E, L-allose) or breast tumor versus 'normal' breast (FIG. 5F, L-xylose).

In summary, the sugars identified herein impart remarkable cell line selectivities (up to a greater than or equal to an eight-fold increased selective uptake in tumor versus normal cell lines in 1 hr) and are far superior (up to greater than or equal to a 10-fold increased uptake in 1 hr versus the 'standard' D-glucose conjugate) to the conventional sugars (D-glucose, 2-deoxy-D-glucose or FDG) employed for uptake enhancement.

While the method of the present invention is described herein as used to identify and assess enhanced conjugates for cancer treatment and prevention, the method and composition of the present invention may also be used to identify and assess enhanced conjugates for other issues as well. For instance, the invention may be used to probe for the best sugars to enhance oral bioavailability and/or gut uptake and thereby enhance oral bioavailability/uptake of drugs, such as with standard Caco-2 monolayers. In addition, the invention may be used to probe for the best sugars for targeting specific bacterial pathogens (e.g. via screening for uptake into different bacterial pathogens) and thereby sugar target antibiotics. Similarly, the invention may be used to probe for the impact of sugars upon whole body distribution. Finally, the present invention may be use used to provide a convenient HT assay for GLUTs or SGLTs. The inhibition of GLUTs are known to kill cancer cells and the inhibition of SGLTs are relevant to reduction of sugar uptake (e.g. for diabetes drugs) or even anti-parasite/viral drug development.

It is understood that the invention is not confined to the specific reagents, formulations, reaction conditions, etc., herein illustrated and described, but embraces such modified forms thereof as come within the scope of the following claims. Other embodiments and uses of the invention will be apparent to those skilled in the art from consideration from the specification and practice of the invention disclosed herein, as well as from the attached pages, which are incorporated by reference herein. All references cited herein for any reason, including all journal citations and U.S./foreign patents and patent applications, are specifically and entirely incorporated herein by reference.

We claim:

1. A method for assaying sugar-mediated transport of glycoconjugates contained in a glycorandomized library that occurs via one or more facilitative glucose transporters (GLUTs), comprising:
   (a) providing a glycorandomized library comprising glycoconjugates with different attached sugars, wherein the glycoconjugates are sufficiently small to be capable of directly passing through the cell membrane of a cell utilizing one or more GLUTs;
   (b) contacting each of said glycoconjugates with cells under conditions to allow uptake of the glycoconjugates into the cells; and
   (c) assessing uptake of said glycoconjugates into the cells, wherein the cells are cancerous, wherein sugar-mediated transport of the glycoconjugates into the cells is quantified relative to a corresponding conjugate lacking the attached sugars.

2. A method for assaying sugar-mediated transport of glycoconjugates contained in a glycorandomized library that occurs via one or more facilitative glucose transporters (GLUTs), comprising:
   (a) providing a glycorandomized library comprising glycoconjugates with different attached sugars, wherein the glycoconjugates are sugar-fluorophore conjugates and are sufficiently small to be capable of directly passing through the cell membrane of a cell utilizing one or more GLUTs, wherein the sugar-fluorophore is selected from the group consisting of aminofluoroscein, nitrobenzoxadiazole or dansyl chloride;
   (b) contacting each of said glycoconjugates with cells under conditions to allow uptake of the glycoconjugates into the cells; and
   (c) assessing uptake of said glycoconjugates into the cells, wherein the cells are cancerous, wherein sugar-mediated transport of the glycoconjugates into the cells is quantified relative to a corresponding conjugate lacking the attached sugars.

3. A method for assaying sugar-mediated transport of glycoconjugates contained in a glycorandomized library, comprising:
   (a) providing a glycorandomized library comprising glycoconjugates with different attached sugars, wherein the glycoconjugates each comprise a sugar moiety directly conjugated to a fluorophore;
   (b) contacting each of said glycoconjugates with cells under conditions to allow uptake of the glycoconjugates into the cells; and
   (c) assessing uptake of said glycoconjugates into the cells, wherein the cells are cancerous, wherein sugar-mediated transport of the glycoconjugates into the cells is quantified.

4. A method for assaying sugar-mediated transport of glycoconjugates contained in a glycorandomized library, comprising:
   (a) providing a glycorandomized library comprising glycoconjugates with different attached sugars, wherein the glycoconjugates each comprise a sugar moiety directly conjugated to a fluorophore, wherein the fluorophore is selected from the group consisting of aminofluoroscein, nitrobenzoxadiazole and dansyl chloride glycoconjugates;
   (b) contacting each of said glycoconjugates with cells under conditions to allow uptake of the glycoconjugates into the cells; and
   (c) assessing uptake of said glycoconjugates into the cells, wherein sugar-mediated transport of the glycoconjugates into the cells is quantified.

* * * * *